US00PP24218P2

(12) United States Plant Patent
Hofmann

(10) Patent No.: US PP24,218 P2
(45) Date of Patent: Feb. 4, 2014

(54) ***SALVIA* PLANT NAMED 'S1013-3'**

(50) Latin Name: *Salvia splendens*
Varietal Denomination: S1013-3

(75) Inventor: Silvia Hofmann, Mainz (DE)

(73) Assignee: Innovaplant GmbH & Co. KG, Gensingen (DE)

( * ) Notice: Subject to any disclaimer, the term of this patent is extended or adjusted under 35 U.S.C. 154(b) by 114 days.

(21) Appl. No.: 13/374,938

(22) Filed: Jan. 24, 2012

(51) Int. Cl.
*A01H 5/00* (2006.01)

(52) U.S. Cl.
USPC ..... Plt./475

(58) Field of Classification Search
USPC ..... Plt./475
See application file for complete search history.

(56) References Cited

PUBLICATIONS

Denver Plants *Salvia* 'Sizzler Red', retrieved on Jul. 10, 2013, retrieved from the Internet at <http://www.denverplants.com/annual/html/salvi_sre.htm> 2003, one page.*

* cited by examiner

*Primary Examiner* — June Hwu

(57) ABSTRACT

A new cultivar of *Salvia* plant named 'S1013-3' that is characterized by a large overall size, a large number of sterile red flowers, a long flowering season and a vigorous growth habit.

1 Drawing Sheet

Botanical classification: *Salvia splendens*.
Variety denomination: 'S1013-3'.

BACKGROUND OF THE INVENTION

The present invention relates to a new and distinct cultivar of *Salvia* plant botanically known as *Salvia splendens* and hereinafter referred to by the cultivar name 'S1013-3'.

The new *Salvia* is the product of a planned breeding program conducted by the inventor in Heidesheim, Germany. The objective of the breeding program is to create new *Salvia* cultivars with unique flower colors, sterile flowers and a long flowering season.

'S1013-3' originated from a crossing in the Spring of 2009 of the female or seed parent a proprietary *Salvia* identified as Paul Tet 3 (not patented) and the male or pollen parent a proprietary *Salvia* identified as Rot 1 (not patented). The resulting seeds were subsequently planted and grown. The cultivar 'S1013-3' was selected by the inventor in the Spring of 2010 as a single plant within the progeny of the stated cross in a cultivated area of Heidesheim, Germany.

Asexual reproduction of the new cultivar 'S 1013-3' first occurred by terminal cuttings in the Spring of 2010 in Heidesheim, Germany. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Salvia* cultivar 'S1013-3'. These traits in combination distinguish 'S1013-3' as a new and distinct cultivar apart from other existing known varieties of *Salvia*.

1. *Salvia* 'S1013-3' exhibits a large overall plant size.
2. *Salvia* 'S1013-3' exhibits a large number of sterile red flowers.
3. *Salvia* 'S1013-3' exhibits a long flowering season.

4. *Salvia* 'S1013-3' exhibits a vigorous growth habit.

The closest comparison cultivar is *Salvia* 'Sizzler Red' (not patented). 'S1013-3' is distinguishable from 'Sizzler Red' by the following characteristics:

1. 'S 1013-3' exhibits a larger overall plant size than 'Sizzler Red '. 12 month old plants of 'S1013-3' can reach 55 cm. in height and 120 cm. in width.
2. 'S1013-3' exhibits more vigorous growth.
3. 'S1013-3' has sterile flowers. The seeds of 'Sizzler Red' are fertile.
4. 'S1013-3' has a longer flowering season than 'Sizzler Red'.

'S1013-3' is distinguishable from the female or seed parent *Salvia* Paul Tet 3 by the following characteristics:

1. 'S1013-3' exhibits sterile self cleaning flowers. The seeds of *Salvia* Paul Tet 3 are fertile.
2. 'S1013-3' has a more compact habit.

'S1013-3' is distinguishable from the male or pollen parent *Salvia* Rot 1 by the following characteristics:

1. 'S1013-3' exhibits sterile self cleaning flowers. The seeds of *Salvia* Rot 1 are fertile.
2. 'S1013-3' has a larger overall plant size.

BRIEF DESCRIPTION OF THE DRAWING

The accompanying photograph illustrates the distinguishing traits of *Salvia* 'S1013-3'. The plant in the photograph shows an overall view of a 4 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Salvia* cultivar named 'S1013-3'. Data was collected in Gensingen, Germany from 3 month old glass greenhouse grown plants in 16 cm. diameter containers. The time of year was Winter and the average temperature was 16 degrees Centigrade during the day and 14 degrees Centigrade at night. The light level was 3000 lux for 16 hours per day. No growth retardants were used. Color determinations are in accordance with The Royal Horticultural Society Colour Chart 2007 edition, except where general color terms of ordinary dictionary significance are used. The growing requirements are similar to the species. 'S1013-3' has not been tested under all possible conditions and phenotypic differences may be observed with variations in environmental, climatic, and cultural conditions, however, without any variance in genotype.

Botanical classification: *Salvia splendens* 'S1013-3'.

Annual or perennial: Annual.

Parentage: 'S1013-3' is the product of the female or seed parent *Salvia* Paul Tet 3 and the male or pollen parent *Salvia* Rot I.

Vigor: Strong.

Growth habit: Upright.

Plant shape: Mounding.

Suitable container size: 12-16 cm.

Height: 30 cm. in height.

Diameter: 30 cm. in diameter.

Low temperature tolerance: 0° Centigrade.

High temperature tolerance: 40° Centigrade.

Propagation: Terminal cuttings.

Time to initiate roots in summer: 19 days to initiate roots at 22° Centigrade.

Time to initiate roots in winter: 25 days to initiate roots at 20° Centigrade.

Time to produce a rooted cutting or liner in summer: 25 days at 22° Centigrade.

Time to produce a rooted cutting or liner in winter: 30 days at 20° Centigrade.

Crop time: Approximately 10 weeks.

Root system: Fine and fibrous.

Stem:

*Branching habit*.—Freely branching.
*Basal branching*.—Yes.
*Average number of lateral branches*.—6.
*Pinching*.—Yes.
*Lateral branch dimensions*.—5 mm. in diameter and 25 cm. in length.
*Internode length*.—4 cm.
*Stem shape*.—Square.
*Stem texture*.—Smooth.
*Stem strength*.—Strong.
*Stem color*.—146B.
*Pubescence*.—Absent.

Foliage:

*Leaf arrangement*.—Opposite.
*Compound or single*.—Single.
*Number of leaves per lateral branch*.—6 to 8.
*Leaf shape*.—Deltoid — Lanceolate.
*Leaf apex*.—Apiculate.
*Leaf base*.—Attenuate.
*Leaf dimensions*.—12 cm. in length and 8 cm. in width.
*Texture*.—Glabrous on both surfaces.
*Pubescence*.—None.
*Leaf margin*.—Serrate.
*Venation pattern*.—Laciniate.
*Young leaf color* (*upper surface*).—143A.
*Young leaf color* (*lower surface*).—138B.
*Mature leaf color* (*upper surface*).—147A.
*Mature leaf color* (*lower surface*).—147B.
*Vein color* (*upper surface*).—145B.
*Vein color* (*under surface*).—145C.
*Petiole dimensions*.—6 cm. in length and 3 mm. in diameter.
*Petiole color*.—N187B.
*Petiole texture*.—Smooth.
*Durability of foliage to stress*.—High.

Flower:

*Inflorescence arrangement*.—Apical Raceme.
*Inflorescence dimensions*.—15 to 20 cm. in height and 7 cm. in width.
*Quantity of flowers per inflorescence*.—30 to 40.
*Quantity of flowers per lateral stem*.—30 to 40.
*Quantity of flower buds per lateral stem*.—20.
*Quantity of flowers and buds per plant*.—Average 150.
*Natural flowering season*.—April to October.
*Time to flower*.—12 weeks.
*Rate of flower opening*.—Every 5 days.
*Fragrance*.—None.
*Flower bud length*.—2 cm.
*Flower bud diameter*.—1 cm.
*Flower bud shape*.—Oval.
*Bud color*.—44B.
*Rate of bud opening*.—5 days.
*Flower aspect*.—Outward/drooping.
*Flower shape*.—Bilabiate.
*Flower dimensions*.—1 cm. in diameter and 4.5 cm. in height.
*Flower longevity*.—5 days.
*Number of petals*.—2, bilabiate.
*Fused or unfused*.—Fused.
*Petal arrangement*.—Tubular, base fused.
*Petal shape*.—Ovate.
*Petal texture*.—Smooth on both surfaces, sparse hairs at the end of both lips.
*Petal margin*.—Entire.
*Petal apex*.—Rounded.
*Petal base*.—Fused.
*Petal length*.—Upper lip 10 mm, lower lip 0.5 mm.
*Petal width*.—Upper lip 5 mm, lower lip 8 mm.
*Petal color when opening* (*upper side*).—44B.
*Petal color when opening* (*under side*).—45A.
*Petal color fully opened* (*upper side*).—44B.
*Petal color fully opened* (*under side*).—45A.
*Petal color fading to*.—44B.
*Self-cleaning or persistent*.—Self-cleaning.
*Corolla tube dimensions*.—4 cm. in length and 5 mm. in width.
*Corolla tube color*.—Inner surface 48A, outer surface 46A.

Sepals:

*Sepal arrangement*.—Fused, keeled.
*Number of sepals*.—3.
*Sepal shape*.—Oval.
*Sepal margin*.—Pubescent, entire.
*Sepal apex*.—Acuminate.
*Sepal base*.—Fused.
*Sepal dimensions*.—2.5 cm. in length and 0.9 cm. in width.
*Young sepal color* (*upper side*).—40A.
*Young sepal color* (*under side*).—40A.
*Mature sepal color* (*upper side*).—40A.
*Mature sepal color* (*under side*).—40A.

Calyx:

*Calyx shape*.—Ovate.

*Calyx dimensions*.—2.5 cm. in length and 1.3 cm. in diameter.

Peduncle:

*Peduncle dimensions*.—20 cm. in length and 3 mm. in diameter.

*Peduncle angle*.—0 to 10 degrees from vertical.

*Peduncle strength*.—Strong.

*Peduncle color*.—40B.

Pedicels:

*Pedicel dimensions*.—5 mm. in length and 1 mm. in diameter.

*Pedicel angle*.—80 degrees from stem.

*Pedicel strength*.—Moderate.

*Pedicel color*.—45A.

Reproduction organs:

*Stamen number*.—2.

*Anther shape*.—Rod shaped.

*Anther size*.—4 mm in length and 1 mm in diameter.

*Anther color*.—162B.

*Amount of pollen*.—Low.

*Pollen color*.—162B.

*Pistil number*.—2.

*Pistil length*.—2 mm.

*Stigma shape*.—Filamentous.

*Stigma color*.—39D.

*Style length*.—6 cm.

*Style color*.—39D.

*Ovary color*.—145C.

Fruit: None, sterile.

Disease and pest resistance: Disease and pest resistance has not been observed.

The invention claimed is:

1. A new and distinct variety of *Salvia* plant named 'S1013-3' as described and illustrated.

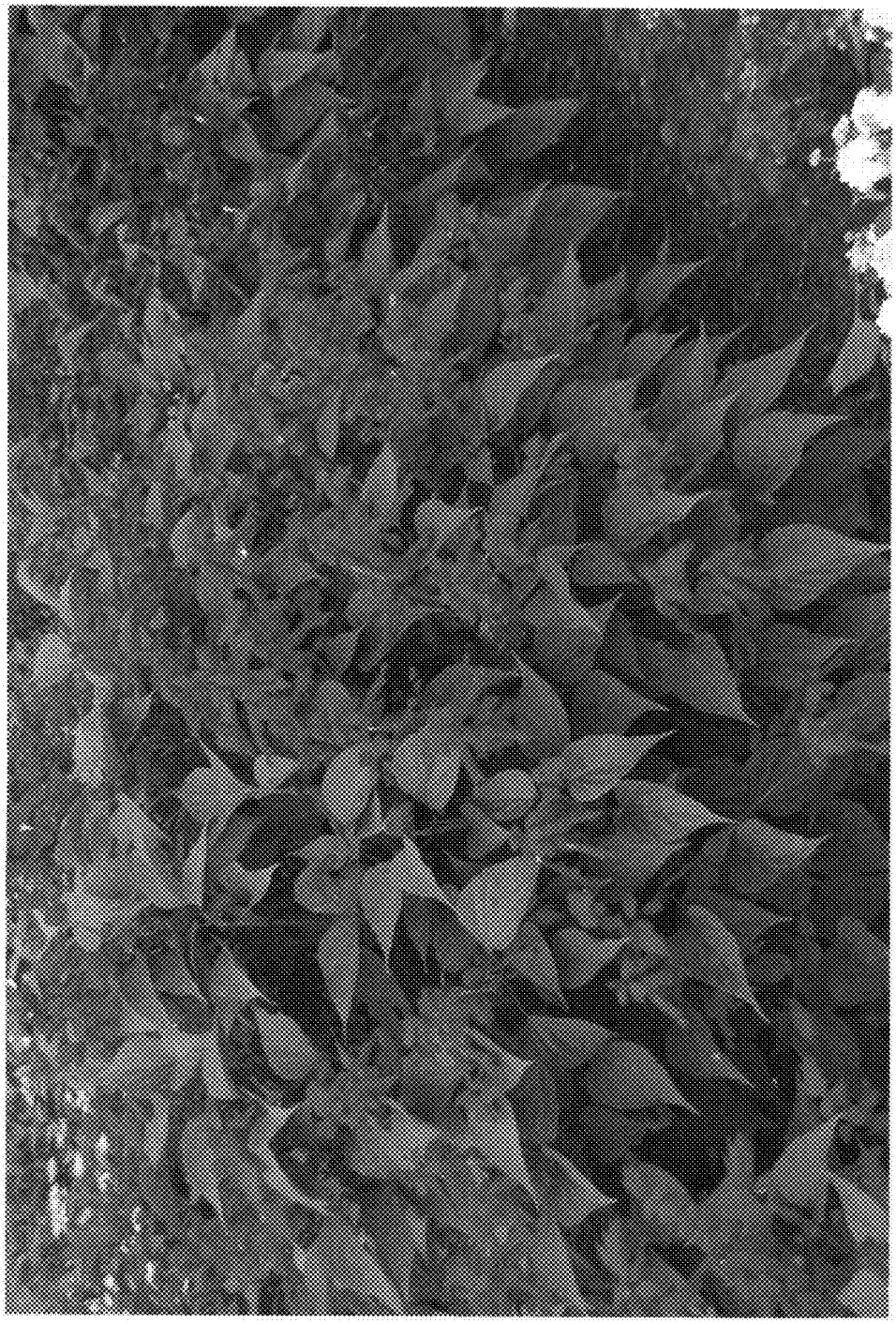

* * * * *